(12) United States Patent  
Kitamura

(10) Patent No.: US 10,695,019 B2  
(45) Date of Patent: Jun. 30, 2020

(54) X-RAY IMAGING SYSTEM

(71) Applicant: Konica Minolta, Inc., Tokyo (JP)

(72) Inventor: Mitsuharu Kitamura, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 49 days.

(21) Appl. No.: 16/257,969

(22) Filed: Jan. 25, 2019

(65) Prior Publication Data

US 2019/0261935 A1    Aug. 29, 2019

(30) Foreign Application Priority Data

Feb. 23, 2018    (JP) ................. 2018-030257

(51) Int. Cl.
| | | |
|---|---|---|
| A61B 6/00 | (2006.01) | |
| G01N 23/041 | (2018.01) | |
| A61B 6/04 | (2006.01) | |
| A61B 6/12 | (2006.01) | |
| G01N 23/04 | (2018.01) | |

(52) U.S. Cl.
CPC ............. *A61B 6/482* (2013.01); *A61B 6/04* (2013.01); *A61B 6/12* (2013.01); *A61B 6/4035* (2013.01); *A61B 6/4291* (2013.01); *A61B 6/4417* (2013.01); *A61B 6/463* (2013.01); *A61B 6/484* (2013.01); *A61B 6/5205* (2013.01); *A61B 6/5235* (2013.01); *A61B 6/545* (2013.01);
(Continued)

(58) Field of Classification Search
CPC .................. A61B 6/484; A61B 6/482
See application file for complete search history.

(56) References Cited

U.S. PATENT DOCUMENTS

| 2014/0341347 A1 | 11/2014 | Radicke |
| 2016/0349197 A1* | 12/2016 | Kitamura ............... G21K 1/06 |
| 2019/0072501 A1* | 3/2019 | Doki .................. A61B 6/4291 |

FOREIGN PATENT DOCUMENTS

| JP | 4445397 B2 | 1/2010 |
| JP | 5652245 B2 | 11/2014 |
| JP | 2016-501630 A | 1/2016 |

OTHER PUBLICATIONS

Dan Stutman, et al., "Talbot Phase-contrast X-ray Imaging for the Small Joint of the Hand," Physics in Medicine and Biology, Aug. 12, 2011, pp. 5697-5720, vol. 56, No. 17, Institute of Physics Publishing, Bristol, GB.

(Continued)

*Primary Examiner* — Dani Fox  
(74) *Attorney, Agent, or Firm* — Lucas & Mercanti, LLP

(57) ABSTRACT

An X-ray imaging system includes an X-ray Talbot imaging apparatus and an image processing apparatus. The image processing apparatus generates reconstruction images from the moire image taken by the X-ray Talbot imaging apparatus. The reconstruction images include a differential phase image, an absorption image and a small-angle scattering image. The X-ray imaging system performs X-ray Talbot imaging and normal X-ray imaging. X-ray Talbot imaging includes setting an exposure energy of the X-ray Talbot imaging apparatus to a first exposure energy and taking the moire image with the X-ray detector. Normal X-ray imaging includes setting the exposure energy of the X-ray Talbot imaging apparatus to a second exposure energy and taking an absorption contrast image with the X-ray detector by normal X-ray imaging.

12 Claims, 5 Drawing Sheets

(52) U.S. Cl.
CPC ............ *G01N 23/041* (2018.02); *A61B 6/502* (2013.01); *G01N 23/04* (2013.01); *G01N 2223/401* (2013.01)

(56) References Cited

OTHER PUBLICATIONS

EPO, Extended European Search Report for the corresponding European Patent Application No. 19151578.2, dated Jul. 19, 2019 (8 pages).

\* cited by examiner

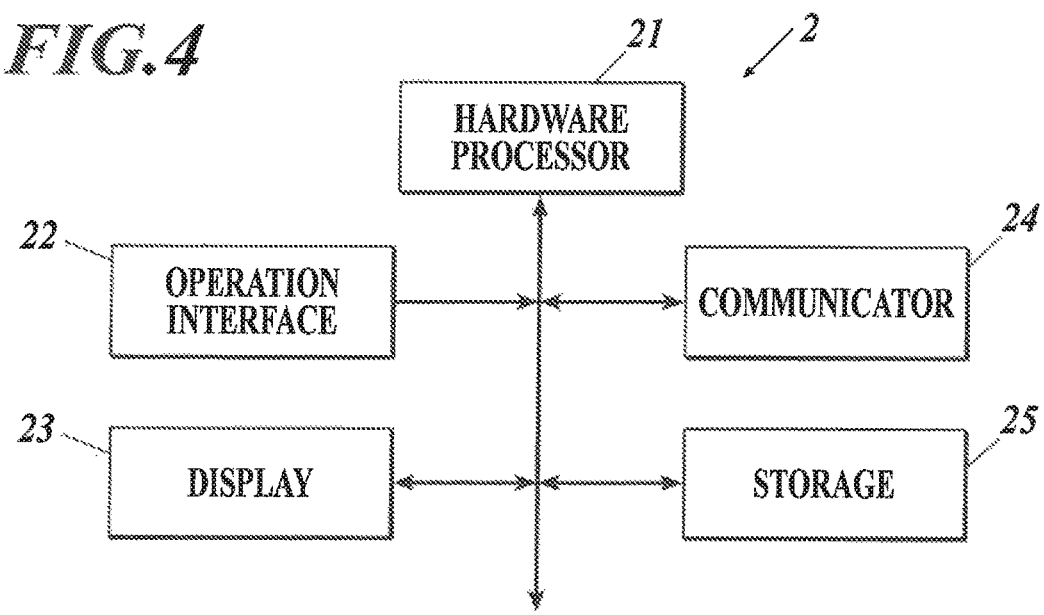
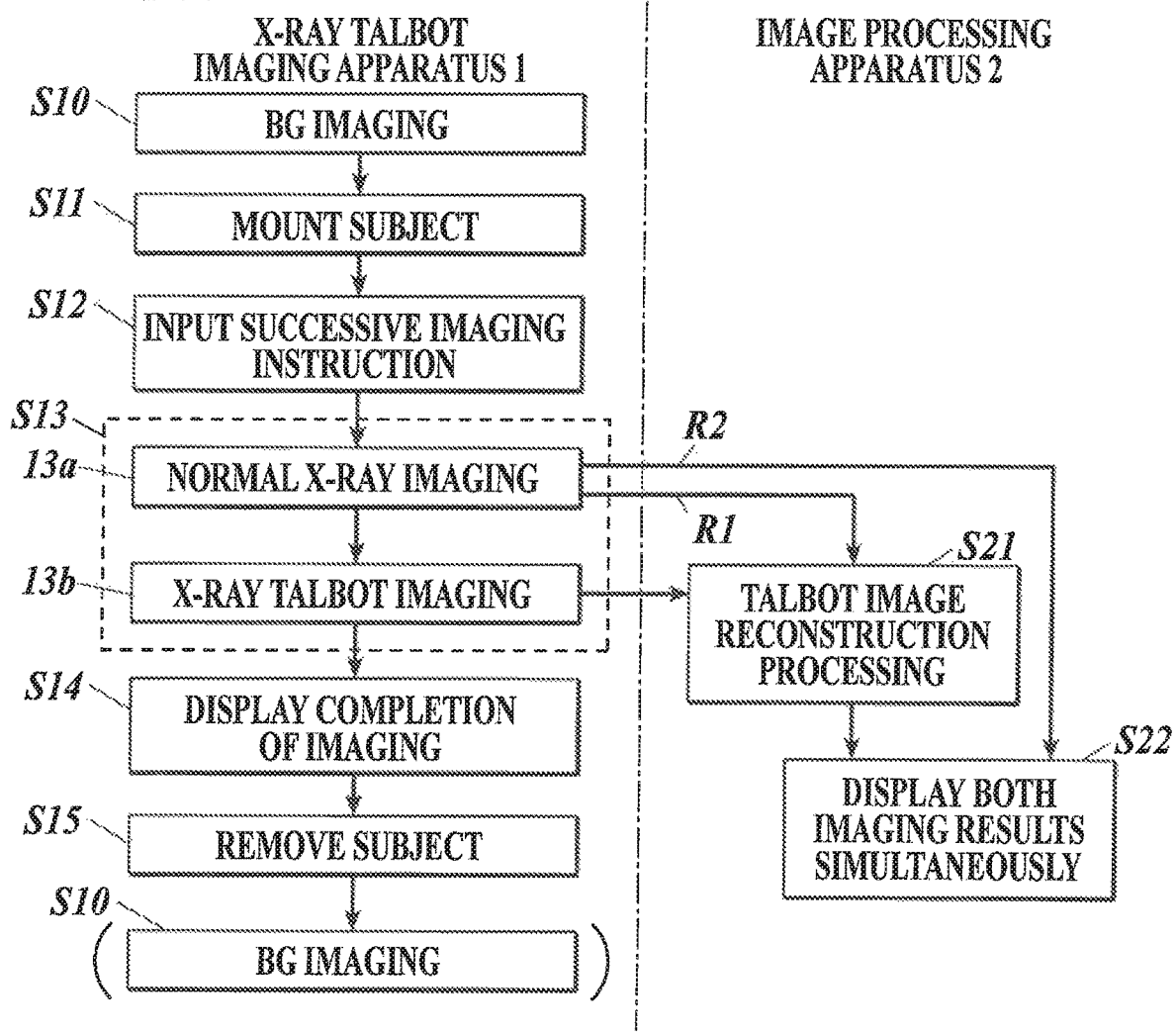

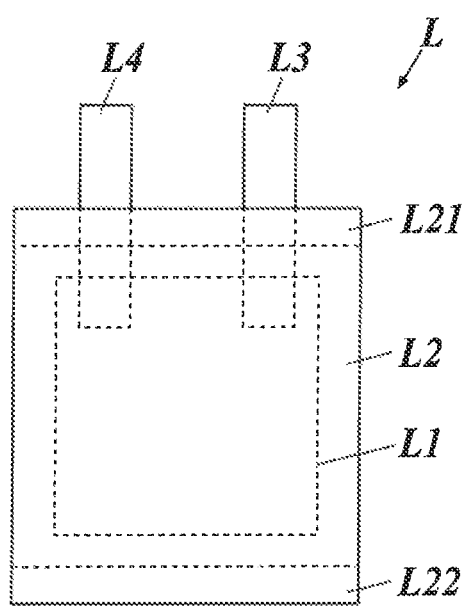

TALBOT ABSORPTION IMAGE

DIFFERENTIAL PHASE IMAGE

SMALL-ANGLE SCATTERING IMAGE

NORMAL ABSORPTION IMAGE (HIGH ENERGY)

X-RAY IMAGING SYSTEM

BACKGROUND

1. Technological Field

The present invention relates to an X-ray imaging system.

2. Description of the Related Art

Almost all X-ray images for medical purposes to make a diagnosis and for non-destructive testing to inspect the inside of an object are based on an absorption contrast technique. The absorption contrast technique is to create contrast according to difference in attenuation of X-ray that passes through a subject. Meanwhile, a phase contrast technique is also used which is to create contrast according to phase change of X-ray instead of absorption of X-ray.

One of phase contrast imaging techniques is a Talbot imaging technique that utilizes the Talbot effect. As an example of the Talbot imaging technique, an X-ray imaging apparatus equipped with a Talbot interferometer or a Talbot-Lau interferometer with a one-dimensional grating (hereinafter referred to as an X-ray Talbot imaging apparatus) has been known in the art. By subjecting a moire image taken with the X-ray Talbot imaging apparatus to reconstruction by an image processing apparatus, it is possible to obtain at least three high-definition reconstruction images of an absorption image, a differential phase image and a small-angle scattering image (e.g. see JP 4445397B). Such X-ray Talbot imaging apparatuses can be used for a variety of subjects such as human bodies, animals and plants and goods to be subjected to non-destructive testing.

The amount of exposure energy required to produce the Talbot effect in an X-ray Talbot imaging apparatus is determined by the configuration of its interferometer.

In the invention disclosed in JP 2016-501630A, two X-ray Talbot radiographic images are obtained with the same interferometer configuration at two different beam energies.

For example, assuming that an X-ray Talbot imaging apparatus is used as a non-destructive testing apparatus for goods such as cells.

While X-ray Talbot imaging is not likely to detect an absorptive substance (e.g. metal) inside a non-transmissive subject, a normal X-ray imaging apparatus based on the absorption contrast technique can often detect such a subject at an exposure energy different from that of the X-ray Talbot imaging.

However, it is troublesome to move a subject between an X-ray Talbot imaging apparatus and a normal X-ray imaging apparatus and to operate them individually. Furthermore, since the subject is moved, the position of the subject in the field of view is different between an image obtained by the X-ray Talbot imaging and an image obtained by the normal X-ray imaging, and it is difficult to compare the images.

SUMMARY

It is an object of the present invention to obtain a normal X-ray radiographic image by using an X-ray Talbot imaging apparatus in addition to an X-ray Talbot radiographic image.

To achieve at least one of the abovementioned objects, according to an aspect of the present invention, an X-ray imaging system includes:

an X-ray Talbot imaging apparatus which includes an X-ray source, a plurality of gratings and an X-ray detector aligned in an X-ray radiation axis and which emits an X-ray from the X-ray source to the X-ray detector through a subject and the plurality of gratings to take a moire image with the X-ray detector; and an image processing apparatus which generates a plurality of reconstruction images from the moire image taken by the X-ray Talbot imaging apparatus, in which the plurality of reconstruction images includes at least three images of a differential phase image, an absorption image and a small-angle scattering image, wherein the X-ray imaging system performs:

X-ray Talbot imaging which includes setting au exposure energy of the X-ray Talbot imaging apparatus to a first exposure energy and taking the moire image with the X-ray detector; and normal X-ray imaging which includes setting the exposure energy of the X-ray Talbot imaging apparatus to a second exposure energy different from the first exposure energy and taking an absorption contrast image with the X-ray detector by normal X-ray imaging.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 4 is a block diagram of the functional configuration of an image processing apparatus.

FIG. 5 is a flowchart including a process of successive imaging of X-ray Talbot imaging and normal X-ray imaging.

FIG. 6 is a schematic view of a lithium-ion cell as an example subject.

FIG. 6 is radiographed.

DETAILED DESCRIPTION OF EMBODIMENTS

Hereinafter, one or more embodiment of the present invention will be described with reference to the drawings. However, the scope of the invention is not limited to the disclosed embodiments.

The embodiment illustrates an X-ray imaging system in which an X-ray Talbot imaging apparatus 1 radiographs a subject 30, and an image processing apparatus 2 generates a plurality of reconstruction images, including at least three reconstruction images of an absorption image, a differential phase image and a small-angle scattering image, from a moire image taken by the X-ray Talbot imaging apparatus 1. Further, the X-ray imaging system is also used to obtain a normal X-ray radiographic image. Examples of the subject 30 include human bodies (mainly for medical purposes), animals and plants, and goods to be subjected to non-destructive testing.

As the X-ray Talbot imaging apparatus 1 in this embodiment, one that includes a Talbot-Lau interferometer provided with a source grating (also referred to as "multi-grating", "multi-slit", "G0 grating", or the like) 12 is employed. An X-ray Talbot imaging apparatus including a Talbot interferometer provided with only a first grating (also referred to as "G1 grating") 14 and a second grating (also referred to as "G2 grating") 15 instead of the source grating 12 may also be employed.

X-Ray Talbot Imaging Apparatus

Figure 1:
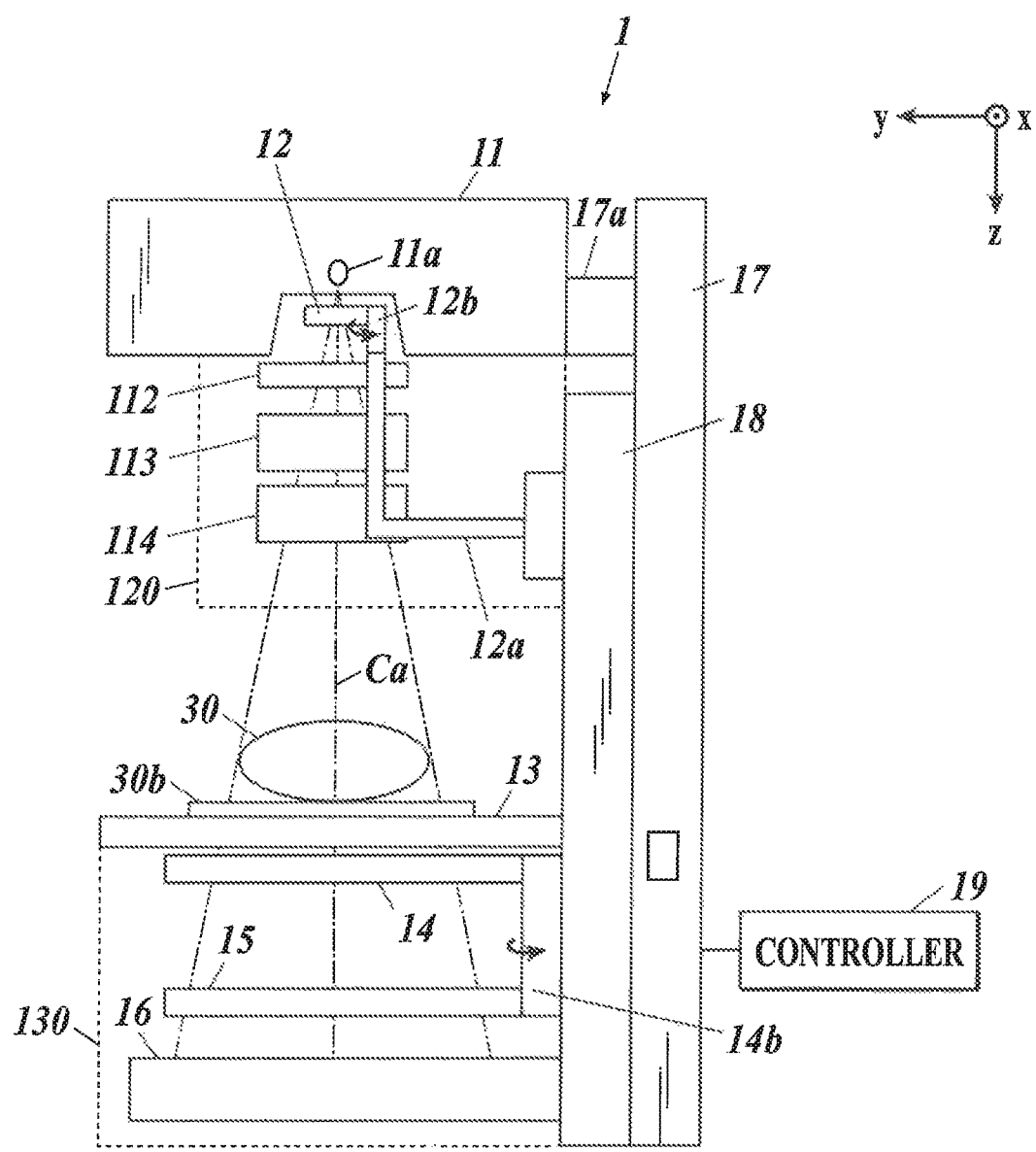
FIG. 1 is a schematic view of an overall picture of an X-ray Talbot imaging apparatus.

FIG. 1 is a schematic view showing an overall picture of the X-ray Talbot imaging apparatus 1 according to this embodiment.

The X-ray Talbot imaging apparatus 1 according to this embodiment includes an X-ray generator 11, the source grating 12, a subject table 13, the first grating 14, the second grating 15, and X-ray detector 16, a support 17, and a base 18.

According to such an X-ray Talbot imaging apparatus 1, a moire image of the subject 30 disposed at a predetermined position with respect to the subject table 13 is taken by a method based on the principle of a fringe scanning technique, or the moire image is analyzed by the Fourier transform, so that at least three types of images are reconstructed (referred to as "reconstruction images"). The three types of images are an absorption image obtained by imaging an average component of moire fringes in the moire image, a different phase image obtained by imaging phase information of the moire fringes, and a small-angle scattering image obtained by imaging visibility of the moire fringes. Resynthesis or the like of these three types of reconstruction images may form more kinds of images.

The fringe scanning technique is a method to obtain a high-resolution reconstruction image by shifting one of a plurality of gratings in a direction of a slit pitch in increments of 1/M (M is a positive integer, where M>2 in an absorption image, and M<3 in a differential phase image and a small-angle scattering image) of the slit pitch of the grating, and by performing reconstruction with a moire image taken M times.

The Fourier transform is a method to reconstruct and form a differential phase image or the like by imaging one moire image with an X-ray Talbot imaging apparatus, with the presence of a subject, and by performing the Fourier transform or the like on the moire image during the image processing. See WO10/050483A for example.

First, the principle common to a Talbot interferometer and a Talbot-Lau interferometer will be described with reference to FIG. 2.

Figure 2:
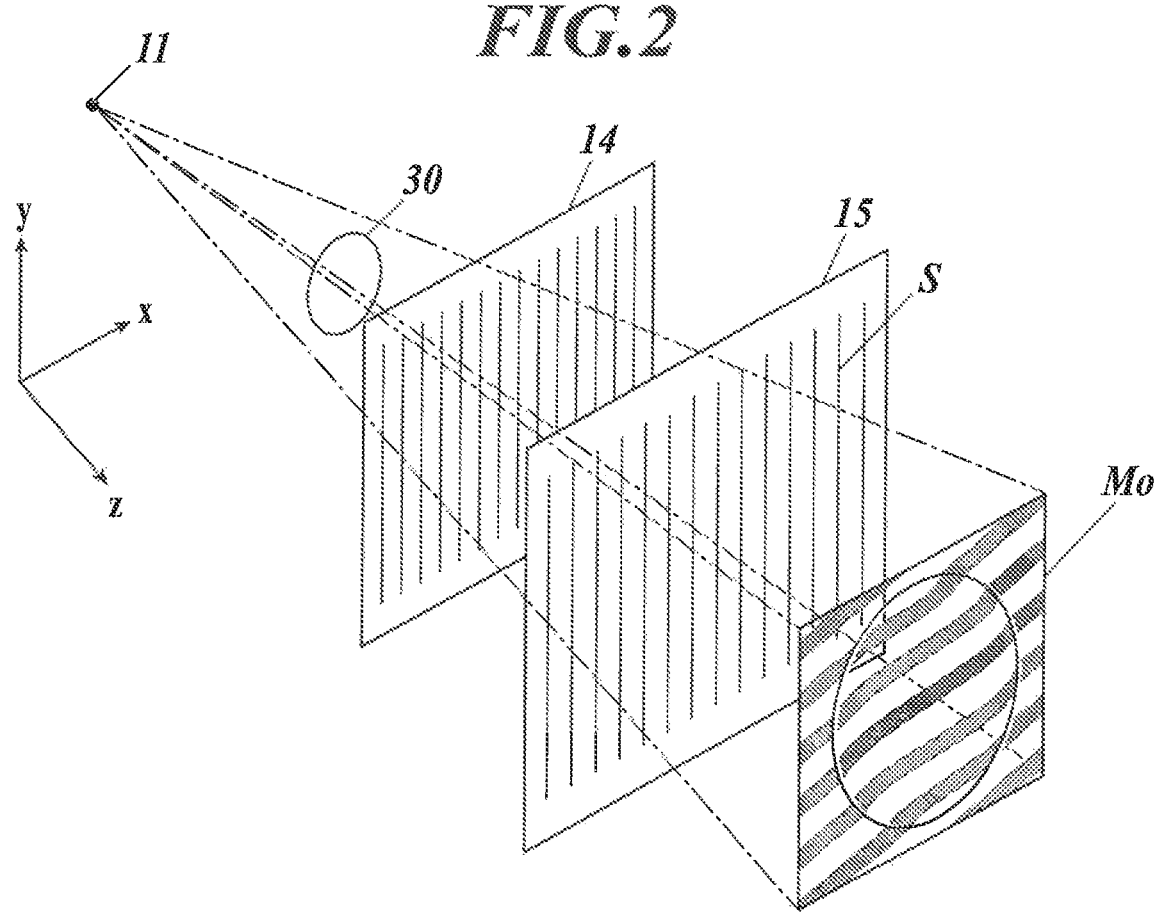
FIG. 2 illustrates the principle of a Talbot interferometer.

FIG. 2 shows a case where a Talbot interferometer is employed. Note that a case where a Talbot-Lau interferometer is employed is described basically similarly. The z direction in FIG. 2 corresponds to the vertical direction in the X-ray Talbot imaging apparatus 1 of FIG. 1, the x and y directions in FIG. 2 correspond to the horizontal directions (front-back, right-left directions) in the X-ray Talbot imaging apparatus 1 of FIG. 1.

Figure 3:
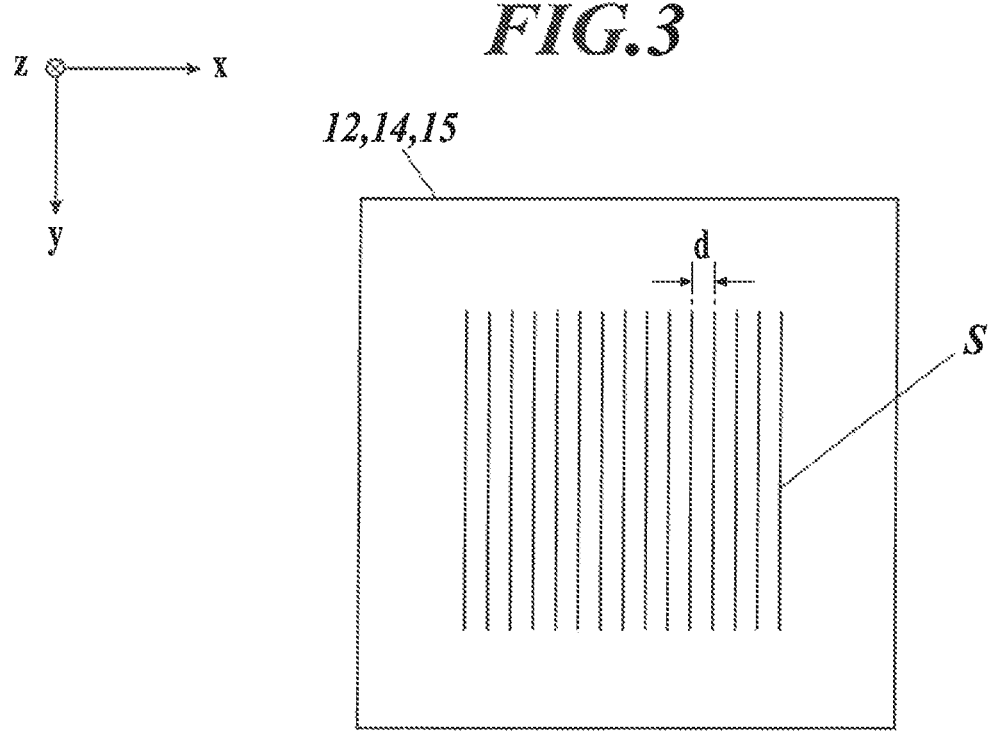
FIG. 3 is a schematic plan view of a source grating, a first grating, and a second grating.

As shown in FIG. 3, the first grating 14 and the second grating 15 (as well as the source grating 12 in a Talbot-Lau interferometer) include a plurality of slits S arranged at a predetermined pitch d in the x direction perpendicular to the z direction which is a direction of X-ray radiation. The slits S are long in the y direction.

As shown in FIG. 1 and FIG. 2, an X-ray emitted from an X-ray source 11a is transmitted through the first grating 14 (in a Talbot-Lau interferometer, the X-ray emitted from the X-ray source 11a is converted to multiple light by the source grating 12 (not shown in FIG. 2)). The transmitted X-ray forms an image at a constant interval in the z direction. This image is called "self-image" (also referred to as "grating image" or the like), and a phenomenon in which a self-image is formed at a constant interval in the z direction is called "Talbot effect."

In other words, the Talbot effect indicates a phenomenon in which coherent light penetrates the first grating 14 provided with the slits S at the constant pitch d, as shown in FIG. 2, causing the light to form a self-image at a constant interval in a light traveling direction.

As shown in FIG. 2, the second grating 15 provided with slits S, as in the first grating 14, is disposed at a position where a self-image of the first grating 14 is formed. When the second grating 15 is arranged in such a manner that an extending direction of the slits S of the second grating 15 (that is, the x-axial direction in FIG. 2) becomes substantially parallel to an extending direction of the slits S of the first grating 14, a moire image Mo is obtained on the second grating 15.

In FIG. 2, if the moire image Mo is drawn on the second grating 15, moire fringes and the slits S are mixed up, making the drawing complicated. Therefore, the moire image Mo is drawn as being separated from the second grating 15. However, actually, the moire image Mo is formed on the second grating 15 and downstream of the second grating 15. The moire image Mo is taken by the X-ray detector 16 disposed immediately below the second grating 15.

As shown in FIG. 2, when the subject 30 is present between the X-ray source 11a and the first grating 14, i.e. on the subject table 13 in FIG. 1, the phase of the X-ray is shifted due to the subject 30. This phase shift wobbles the moire fringes of the moire image Mo from the edge of the subject 30. On the other hand, if the subject 30 is not present between the X-ray source 11a and the first grating 14, which is not shown in the drawing, the moire image Mo with only the moire fringes shows up. This is the principle of a Talbot interferometer and a Talbot-Lau interferometer.

Based on this principle, in the X-ray Talbot imaging apparatus 1 according to this embodiment, as shown in FIG. 1, for example, the second grating 15 is disposed at a position inside a second cover unit 130 where the self-image of the first grating 14 is formed. As described above, separating the second grating 15 and the X-ray detector 16 blurs the moire image Mo (see FIG. 2). Therefore, in this embodiment, the X-ray detector 16 is disposed immediately below the second grating 15.

The second cover unit 130 is provided to protect the first grating 14, the second grating 15, the X-ray detector 16, and the like so that somebody or something does not hit or touch the X-ray detector 16 and the like.

The second grating 15 may be formed of an emitting material such as a scintillator or amorphous selenium, and the second grating 15 may be formed in an integrated manner with the X-ray detector 16.

Although not shown in the drawing, the X-ray detector 16 includes conversion elements that generate electric signals depending on emitted X-rays. The conversion elements are arranged two-dimensionally (in matrix form), and the electric signals generated by the conversion elements are read as image signals. In this embodiment, the X-ray detector 16 is configured to take the moire Mo, or the X-ray image formed on the second grating 15, as an image signal for each conversion element. The pixel size of the X-ray detector 16 is 10 to 300 (μm), and preferably, 50 to 200 (μm).

An example of the X-ray detector 16 may include a flat panel detector (FPD). There are an indirect conversion FPD that converts a detected X-ray into an electric signal through a photoelectric conversion element; and a direct conversion FPD that directly converts a detected X-ray into an electric signal. Either FPD is employable.

In an indirect conversion FPD, photoelectric conversion elements that form a pixel are two-dimensionally arranged together with a thin film transistor (TFT) under a scintillator plate made of CsI, Gd2O2S, or the like. When an X-ray incident on the X-ray detector 16 is absorbed by the scintillator plate, the scintillator plate emits light. The emitted light leads to accumulation of charges in each photoelectric conversion element, and the accumulated charges are read out as image signals.

In direct conversion FPD, an amorphous selenium film having a film thickness of 100 to 100 (μm) is formed on glass by thermal evaporation of amorphous selenium, and the amorphous selenium film and electrodes are evaporated on an array of the two-dimensionally arranged TFT. When the amorphous selenium film absorbs an X-ray, a voltage is liberated in the substance in the form of electron-hole pairs, and a voltage signal between the electrodes is read by the TFT.

Imaging units such as a charge coupled device (CCD) and an X-ray camera may also be used as the X-ray detector 16.

In this embodiment, the X-ray Talbot imaging apparatus 1 takes a plurality of moire images Mo by what is called a fringe scanning technique. In other words, the X-ray Talbot imaging apparatus 1 according to this embodiment takes the plurality of moire images Mo by shifting relative positions of the first grating 14 and the second grating 15 in the x-axial direction in FIGS. 1 to 3 (that is, a direction perpendicular to the extending direction of the slits S (y-axial direction)).

An image processing apparatus 2 which has received image signals of the plurality of moire images Mo from the X-ray Talbot imaging apparatus 1 executes image processing and reconstructs an absorption image, a differential phase image, a small-angle scattering image, and the like based on the plurality of moire images Mo.

To take the plurality of moire images Mo with the X-ray Talbot imaging apparatus 1 according to the present embodiment by the fringe scanning technique, a shifting device (not shown) for shifting the first grating 14 in the y-axial direction in increments of a predetermined distance is provided. The X-ray Talbot imaging apparatus 1 may move the second grating 15, instead of the first grating 14, or may move both gratings in the x-axial direction.

While fixing the relative positions of the first grating 14 and the second grating 15, the X-ray Talbot imaging apparatus 1 may take one moire image Mo, and this moire image Mo may be analyzed by the Fourier transform in the image processing executed by the image processing apparatus 2 to reconstruct an absorption image, a differential phase image, and the like.

Hereinafter described is configurations of other parts in the X-ray Talbot imaging apparatus 1 according to this embodiment. The X-ray Talbot imaging apparatus 1 in this embodiment is of what is called vertical type and includes the X-ray generator 11, the source grating 12, the subject table 13, the first grating 14, the second grating 15, and the X-ray detector 16 arranged in this order in the z direction or the gravity direction. In other words, in this embodiment, the z direction is the direction of X-ray radiation from the X-ray generator 11.

As the X-ray source 11a, the X-ray generator 11 includes, for example, a Coolidge X-ray source, a rotating anode X-ray source or the like, either of which is widely and generally used in a medical field. Other X-ray sources may also be employed herein. The X-ray generator 11 in this embodiment emits an X-ray in a cone-beam shape from a focal point. In other words, the X-ray is emitted in such a manner that the X-ray spreads out as it separates from the X-ray generator 11.

In this embodiment, the source grating 12 is provided below the X-ray generator 11. In regard to vibration of the X-ray generator 11 caused by rotation of an anode in the X-ray source 11a, in order not to transmit the vibration to the source grating 12, the source grating 12 in this embodiment is not attached to the X-ray generator 11 but to a fixing member 12a that is attached to the base 18 provided on the support 17.

In this embodiment, the source grating 12 is provided below the X-ray generator 11. In regard to vibration of the X-ray generator 11 caused by rotation of an anode in the X-ray source 11a, in order not to transmit the vibration to the source grating 12, the source grating 12 in this embodiment is not attached to the X-ray generator 11 but to a fixing member 12a that is attached to the base 18 provided on the support 17.

In this embodiment, in order to prevent propagation of the vibration of the X-ray generator 11 to other parts of the X-ray Talbot imaging apparatus 1 such as the support 17 (or to reduce the vibration to be propagated), a cushioning member 17a is provided between the X-ray generator 11 and the support 17.

In this embodiment, in addition to the source grating 12, to the fixing member 12a, attached are a filter (also referred to as "additional filter") 112 that changes the quality of an X-ray transmitted through the source grating 12, a beam limiting device 113 that limits an irradiation field of an X-ray to be emitted, and an irradiation field lamp 114 that irradiates a subject with visible light instead of an X-ray before X-ray radiation so as to adjust a position of the X-ray.

The source grating 12, the filter 112, and the beam lighting device 113 are not necessarily disposed in this order. Furthermore, in this embodiment, a first cover unit 120 that protects the source grating 12 and the like is disposed around those members.

In this embodiment, the controller 19 (see FIG. 1) includes a computer in which a central processing unit (CPU), a read only memory (ROM), a random access memory (RAM), an input/output interface, and the like are connected to each other by a bus (those members are not shown in the drawing). Instead of a general-purpose computer as in this embodiment, the controller 19 may include a dedicated control device. The controller 19 is provided with appropriate units and devices such as an input unit and an output unit including an operation interface, a storage, and a communicator.

The controller 19 perform overall control of the X-ray Talbot imaging apparatus 1. In other words, for example, the controller 19 is connected to the X-ray generator 11 and may set a tube voltage, a tube current, an irradiation time, and the like in the X-ray source 11a. The controller 19, for example, may also be configured to relay transmission and reception of signals and data between the X-ray detector 16 and the image processing apparatus 2 or the like.

When the X-ray Talbot imaging apparatus 1 is configured to take the plurality of moire images Mo by the fringe scanning technique as in the present embodiment, the controller 19 is configured to control the shifting device so as to adjust the predetermined moving distance of the first grating 14 (or the second grating 15 or both) and to adjust the timing of shifting the grating(s) and emitting the X-ray from the X-ray generator 11.

The controller 19 is connected to the image processing apparatus 2 (described in detail later) through a network such as a LAN (Local Area Network).

While the controller 19 and the image processing apparatus 2 are configured as individual devices in the embodiment, they can be configured as a single device. Further, a generator (not shown) for controlling the X-ray generator 11 may be provided separately from the controller 19. That is, the configuration of the controller 19, the image processing apparatus 2, the generator of the X-ray generator 11 and the like can be suitably selected with regard to whether two or more of them are configured as a single device or they are configured as individual devices.

In the above-described storage or the ROM, setting of the X-ray source 11a of the X-ray generator 11 such as a tube voltage, a tube current and an irradiation time, various data necessary for adjusting the timing of shifting the gratings and emitting the X-ray from the X-ray generator 11 and the like, processing programs necessary for performing various processing and the like are stored.

Image Processing Apparatus

The image processing apparatus 2 can generate the three high-definition reconstruction images (absorption image, differential phase image, small-angle scattering image) of the subject 30 from the moire images obtained by the X-ray Talbot imaging apparatus 1. The image processing apparatus 2 can also perform image processing on the obtained reconstruction images. As illustrated in FIG. 4, the image processing apparatus 2 includes a hardware processor 21, an operation interface 22, a display 23, a communicator 24 and a storage 25.

The hardware processor 21 includes a CPU (Central Processing Unit), a RAM (Random Access Memory) and the like. The hardware processor 21 performs a variety of processing such as image generation processing, image display processing and association processing (described later) in cooperation with programs stored in the storage 25.

The operation interface 22 includes a keyboard with cursor keys, number input keys and a variety of function keys and a pointing device such as a mouse. The operation interface 22 outputs a signal corresponding to a key operation on the keyboard or a mouse operation to the hardware processor 21. Further, the operation interface 22 may include a touch panel that is provided integrally with a display of the display 23. In this case, the operation interface 22 generates and outputs a signal to the hardware processor 21 according to an operation made on the touch panel.

For example, the display 23 includes a display such as a CRT (Cathode Ray Tube) or an LCD (Liquid Crystal Display). The display 23 is controlled by the hardware processor 21 to display an operation screen, the operation status of the X-ray Talbot imaging apparatus 1, the generated reconstruction images and the like.

The communicator 24, which includes a communication interface, communicates with the X-ray Talbot imaging apparatus 1 and an external management system such as a data management system including a cloud computer or a PACS (Picture Archiving and Communication System) in a communication network in a wireless or wired manner.

In the storage 25, programs to be executed by the hardware processor 21 and data necessary for executing the programs are stored. The storage 25 can store the moire images taken by the X-ray Talbot imaging apparatus 1 or the reconstruction images generated by the image processing apparatus 2 by associating them with prestored supplementary information data on the subject 30. The supplementary information data may be stored in either the storage 25 or the management system such as a data management system or a PACS.

When the subject 30 is a human body, the stored supplementary information data includes basic information such as radiographic data, a patient name and subject information (a part to be diagnosed (radiographic part) or a combination of a part to be diagnosed and possible diseases names as the part). In addition, the supplementary information data may also include information for identifying a patient such as a patient-unique ID.

When the subject 30 is goods to be subjected to non-destructive testing, the stored supplementary information data includes actual data representing the surface shape of a sample (not shown) that is formed in the same way as the subject 30 or design data that can specify the surface shape. To be more specific, for example, the actual data represents an CT image of a sample of the subject 30 or a result of measurement with a three-dimensional measurement device. The design data may be mechanical design data, mechanical CAD data or the like.

The X-ray Talbot imaging apparatus 1 includes a rotator 30b that rotates the subject 30 around the X-ray radiation axis Ca. When the subject 30 is rotated to a certain angle by the rotator 30b, an image of the subject 30 taken after the rotation is different from an image of the subject 30 taken before rotation. That is, a part of the subject 30 that has been hidden before the rotation may sometimes come up in the image taken after the rotation.

A center part (radiographic area) of the rotator 30b on which the subject 30 is mounted is composed of only a material with high X-ray transmissivity.

The rotation of the rotator 30b can be automatically controlled in synchronization with the X-ray Talbot imaging apparatus 1 by the controller 19 of the X-ray Talbot imaging apparatus 1. That is, the controller 19 is connected to a driver of the rotator so that communication is possible.

The image generation processing is performed by the hardware processor 21 in cooperation with an image generating program stored in the storage 25. Specifically, the three reconstruction images (absorption image, differential phase image and small-angle scattering image) can be generated from the moire images Mo taken by the X-ray Talbot imaging apparatus 1.

The image display processing is performed by the hardware processor 21 in cooperation with an image displaying program stored in the storage 25. Specifically, as illustrated in FIG. 7A to FIG. 7D, the three reconstruction images and an image from normal X-ray imaging can be displayed in the same size. That is, the four images with different appearances can be displayed side by side at the same time or overlaid or cross-faded in the same position. When the subject 30 is radiographed at different angles by using the rotator 30b in the X-ray Talbot imaging, the respective images are included in the three reconstruction images. In contrast, in the normal X-ray imaging described below, it is only necessary to radiograph the subject 30 at any one of the angles.

Normal X-Ray Imaging

The normal X-ray imaging is performed by the following two methods.

First Method

A first exposure energy for the X-ray Talbot imaging of the X-ray Talbot imaging apparatus 1 is determined by the configuration of its interferometer, which is referred to as a Talbot interferometer design energy. It is possible to form a self-image at the G2 grating (second grating 15) to obtain Talbot image at an energy of 1 or ½ time the Talbot interferometer design energy. (It is principally possible to form an image even at an energy of three or four times the Talbot interferometer design energy, but it is practically impossible to obtain an image due to the weakness of a signal.)

Accordingly, a second exposure energy for the normal X-ray imaging is selected so as not to be at a level at which a phase contrast image is obtained. That is, the second exposure energy is not equal to n times (n being an integer) or 1/n time (n being an integer) the first exposure energy.

The exposure energy can be controlled by changing the tube voltage of the X-ray source 11a and the exposure time.

This method is referred to as a first method.

Second Method

A second method involves emitting an X-ray from the X-ray source 11a to the X-ray detector 16 through the subject 30 without intervention of the gratings 12, 14, 14.

When this method is used, the X-ray Talbot imaging apparatus 1 includes a retractors 12b, 14b that retract the gratings 12, 14, 15 from the X-ray path. The retractors 12b, 14b, which have a mechanism of moving the gratings 12, 14, 15 in the x-y plane, are controlled by the controller 19.

The plurality of gratings 12, 14, 15 are retracted from the X-ray path by the retractors 12b, 14b, and the exposure energy of the X-ray Talbot imaging apparatus 1 is set to the second exposure energy. An X-ray is emitted from the X-ray source 11a to the X-ray detector 16 through the subject 30 so that an absorption contract image is taken with the X-ray detector 16 by the normal X-ray imaging.

In this method, the second exposure energy is arbitrarily selected, which may be at the same level as the first exposure energy.

Successive Imaging

Next, a process of successive imaging will be described. The flowchart thereof is shown in FIG. 5.

First, an operator amounts the subject 30 on the X-ray Talbot imaging apparatus 1 as illustrated in FIG. 1 (S11) and then inputs a successive imaging instruction to the controller 19 to successively perform the X-ray Talbot imaging and the normal X-ray imaging (S12).

Once the controller 19 receives the successive imaging instruction, it controls the X-ray Talbot imaging apparatus 1 to successively perform the X-ray Talbot imaging 13b and the normal X-ray imaging 13a without any intervention of an imaging instruction from the operator between the X-ray Talbot imaging and the normal X-ray imaging (performs successive imaging S13).

Depending on a preset process, the controller 19 controls the rotator 30b to rotate the subject 30 to a different angle and performs the X-ray Talbot imaging 13b at each angle.

When the normal X-ray imaging 13a is performed by the first method, the X-ray Talbot imaging apparatus 1 changes the exposure energy. When the normal X-ray imaging 13a is performed by the second method, the controller 19 controls the retractors 12b, 14b to retract the gratings 12, 14, 15 in the normal X-ray imaging 13a and then to put the gratings 12, 14, 15 back after the normal X-ray imaging 13a. In the first method, the second exposure energy is greater than the first exposure energy.

The X-ray Talbot imaging 13b and the normal X-ray imaging 13a may be performed in any order. Before the subject is mounted or after the subject is removed, the X-ray Talbot imaging apparatus 1 performs background imaging S10 to obtain a background image to be used for image processing. When the subject 30 is to be rotated for another imaging or has been rotated, the background imaging S10 is performed at each angle.

After performing the successive imaging S13, the controller 19 displays completion of the imaging to the operator (S14). The operator confirms completion of the imaging and then removes the subject 30 from the X-ray Talbot imaging apparatus 1 (S15).

Meanwhile, the image processing apparatus 2 performs the above-described reconstruction processing S21 on the moire images Mo taken in the X-ray Talbot imaging 13b to generate the three reconstruction images (absorption image, differential phase image, small-angle scattering image).

When the normal X-ray imaging 13a is performed by the first method, the image processing apparatus 2 selects a first route R1 to perform the same above-described reconstruction processing S21 on the image taken in the normal X-ray imaging 13a to generate three reconstruction images (absorption image, differential phase image, small-angle scattering image). Then, the image processing apparatus outputs only the absorption image as the image result. Instead of the reconstruction processing to erase a grating image and a grating-induced moire pattern. An example of such correction processing is differential processing to erase the grating image and additional more unevenness correction as disclosed in JP 5652245B. When the reconstruction processing S21 is performed, it is not necessary to perform additional correction to erase the grating image and the grating-induced moire pattern since the grating image and the moire pattern are erased by the processing.

When the normal X-ray imaging 13a is performed by the second method, the image processing apparatus 2 selects a second route R2 and outputs the absorption image from the normal X-ray imaging 13a as the imaging result.

The image processing apparatus 2 simultaneously displays the three reconstruction images (absorption image, differential phase image, small-angle scattering image) from the X-ray Talbot imaging 13b and the absorption image from the normal X-ray imaging 13a on the display 23 as the imaging results.

FIG. 7A to FIG. 7D illustrate an example of output images when the above-described imaging and image processing were performed on a lithium-ion cell in FIG. 6.

As illustrated in FIG. 6, the lithium-ion cell L as a subject includes a cell main body L1 (including a cathode, a separator, an anode, etc.), an aluminum seater L2 and electrode terminals L3, L4. At ends of the aluminum sealer L2, sealing portions L21, L22 are formed.

Figure 7A:
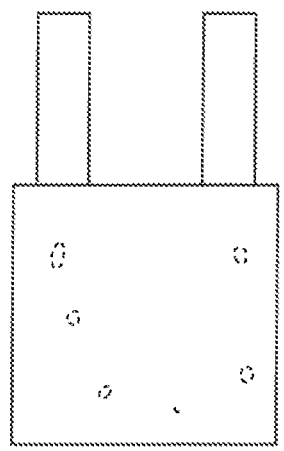
FIG. 7A is a schematic view of an output example of a Talbot absorption image when the lithium-ion cell in FIG. 6 is radiographed.
Figure 7B:
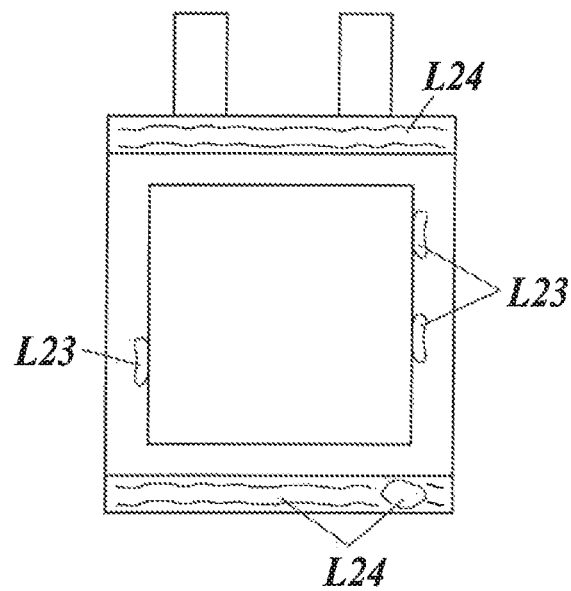
FIG. 7B is a schematic view of an output example of a differential phase image when the lithium-ion cell
Figure 7C:
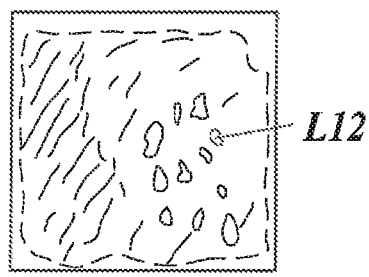
FIG. 7C is a schematic view of an output example of a small-angle scattering image when the lithium-ion cell in FIG. 6 is radiographed.
Figure 7D:
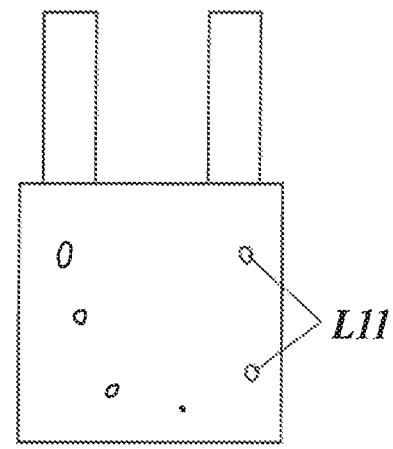
FIG. 7D is a schematic view of an output example of a normal absorption image when the lithium-ion cell in FIG. 6 is radiographed.

Heavy metals (L11) such as a metal foreign matter inside the cell main body L1 were hardly or not visualize din the absorption image from the X-ray Talbot imaging 13b of FIG. 7A but were clearly visualized in the absorption image from the normal X-ray imaging 13a of FIG. 7D, which was taken at high energy.

Lithium precipitates (L12) inside the cell main body L1 were visualized in the small-angle scattering image from the X-ray Talbot imaging 13b of FIG. 7C.

Gases (L23) inside the aluminum sealer L2, local separation of the sealing portions L21, L22, the sealing condition (L24) such as the condition of compression bonding were visualized in the differential phase image from the X-ray Talbot imaging 13b of the FIG. 7B.

As described above, when a heavy metal such as metal foreign matter and a light element substance such as lithium and gas sealing condition are concurrently present in a subject, it is possible to visualize and compare them at the same time in the same position by performing X-ray Talbot imaging and normal X-ray imaging without moving the subject.

Unlike in a medical use, there is no dose limit in non-destructive testing, and successively performing normal X-ray imaging at high dose and X-ray Talbot imaging since does not cause any problem.

Further, neither X-ray Talbot imaging nor normal X-ray imaging require an operation by a licensed person such as a doctor in non-destructive testing, it is possible to perform the successive imaging as described above.

OTHERS AND CONCLUSION

An absorption image can also be obtained in X-ray Talbot imaging. However, when X-ray Talbot imaging is performed at high energy, it is generally required to increase the aspect ratio of gratings used. That is, it is necessary to change the grating design as the exposure energy is increased. It is difficult and limitative to increase the aspect ratio of the micron-order gratings due to technical difficulty in production. On the other hand, some substances and phenomena can be visualized only by a differential phase image or a small-angle scattering image, which are unique to X-ray Talbot imaging. Therefore, it is very meaningful to take these X-ray Talbot radiographic images at the same time with a normal X-ray radiographic image.

The absorption image from the X-ray Talbot imaging 13b in FIG. 7A is taken at such an exposure energy that is available for X-ray Talbot imaging. When a subject has a thick portion or a substance that does not transmit X-ray well, it is difficult to visualize the portion or substance in the absorption image and the other images.

In contrast, another absorption image can be taken independently at higher exposure energy as in the above-described first method as long as an X-ray tube is capable of producing the energy. Successive radiographing allows to obtain such an absorption image (FIG. 7D) that is taken at a high exposure energy in the same position without moving the subject at all and that can be compared with the other images.

It is therefore possible to obtain an absorption image of the thick portion or the inner substance, which has been difficult to be visualized in the prior art.

As described above, a material with high absorption such as metal in a portion with low transmissivity of a subject cannot often be detected by an absorption image (FIG. 7A) from X-ray Talbot imaging that is perform at a specified tube voltage. However, by taking an image at higher tube voltage or higher energy that an X-ray tube can output rather than a voltage or energy suitable for X-ray Talbot imaging, it is possible to improve the detectability. Further, by successively performing the normal X-ray imaging 13a by the first or second method and the X-ray Talbot imaging 13b, it possible to simultaneously detect an item that is detectable only by an image unique to X-ray Talbot imaging.

The first method can be performed without any significant modification in the configuration of the X-ray Talbot imaging apparatus 1 except for providing an X-ray tube that is capable of performing an exposure at high tube voltage and high energy in order to obtain four images as illustrated in FIG. 7A to FIG. 7D. (While it is necessary to add an image processing software and the like, it is not necessary to modify the hardware.)

As described above, by successively radiographing metal and the like, which are more detectable at higher tube voltage, and light metal precipitate, resin and the like, which are detectable by X-ray Talbot imaging, with the same apparatus, it is possible to evaluate many items.

The second exposure energy may be less than the first exposure energy. Such normal X-ray imaging 13a is useful for visualization of a substance in a low-absorption subject or comparison of such substances with a subject visualized in a differential phase image (to distinguish between a bubble and a low-absorption substance).

In the normal X-ray imaging, the second method can eliminate X-ray absorption of the gratings 12, 14, 15, allow the lower X-ray output of the X-ray source 11a and prevent appearance of a grating image or a moire pattern.

By introducing the rotator 30b or the like so that a subject can be radiographed at any angle through the one-dimensional gratings, it is possible to evaluate the orientation (angular dependency) of a structure such as an internal foreign matter or fibers. For example, when the differential phase image (FIG. 7B) includes a plurality of images taken at different angles, it is easier to evaluate the condition of the sealing portions (L21, L22 in the longitudinal direction or the transverse direction. In this case, the normal X-ray imaging can be performed at any angle since it is not affected by the direction of the gratings. To compare the output images, it is preferred to perform the normal X-ray imaging in the course of the X-ray Talbot imaging in which a subject is rotated since the images can be obtained with a less time lag.

With regard to the manner of displaying the four images on the display 23, they may be simultaneously displayed side by side on split screens so that the positional relationship of the subjects visualized in the respective images is also recognizable. Alternatively, they may be sequentially displayed at the same position on a full screen so that details of the images can be checked easily.

While an absorption image is also obtained from the X-ray Talbot imaging, the normal X-ray imaging at higher exposure energy can visualize a substance with high absorption (e.g. metal) in a subject with low transmissivity. In the normal X-ray imaging 13, a plurality of images may be taken at different exposure energies. With different exposure energies, it is possible to obtain images with different visibilities for substances with different absorptions.

Suitable changes can be made in the detailed configuration and the operation of the components of the X-ray imaging system according to the above-described embodiment without departing from the feature of the present invention.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2018-030257, filed on Feb. 23, 2018, is incorporated herein by, reference in its entirety.

What is claimed is:

1. An X-ray imaging system, comprising:
an X-ray Talbot imaging apparatus which includes an X-ray source, a plurality of gratings and an X-ray detector aligned in an X-ray radiation axis and which emits an X-ray from the X-ray source to the X-ray detector through a subject and the plurality of gratings to take a moire image with the X-ray detector; and an image processing apparatus which generates a plurality of reconstruction images from the moire image taken by the X-ray Talbot imaging apparatus, in which the plurality of reconstruction images includes at least three images of a differential phase image, an absorption image and a small-angle scattering image, wherein the X-ray imaging system performs;

X-ray Talbot imaging which includes setting an exposure energy of the X-ray Talbot imaging apparatus to a first exposure energy and taking the moire image with the X-ray detector; and normal X-ray imaging which includes setting the exposure energy of the X-ray Talbot imaging apparatus to a second exposure energy different from the first exposure energy and taking an absorption contrast image with the X-ray detector by normal X-ray imaging.

2. The X-ray imaging system according to claim 1, wherein the second exposure energy is different from n times or 1/n time the first exposure energy, the n being an integer.

3. The X-ray imaging system according to claim 1, wherein a same processing as reconstruction image generation processing for the moire image by the image processing apparatus is performed on an absorption contrast image from the normal X-ray imaging.

4. The X-ray imaging system according to claim 1, further comprising:

a rotator which changes a direction of the subject by rotating the subject about an axis of the X-ray, wherein the plurality of gratings includes a one-dimensional grating.

5. The X-ray imaging system according to claim 1, wherein the plurality of reconstruction images and the image obtained by the normal X-ray imaging are displayed on a screen in a same size.

6. The X-ray imaging system according to claim 1, wherein the second exposure energy is greater than the first exposure energy.

7. The X-ray imaging system according to claim 1, further comprising:

a controller which controls the X-ray Talbot imaging and the normal X imaging, wherein the controller receives from an operator a successive imaging instruction to successively perform the X-ray Talbot imaging and the normal X-ray imaging, and wherein in response to the single successive radiographing instruction, the controller controls the X-ray Talbot imaging apparatus to successively perform the X-ray Talbot imaging and the normal X-ray imaging without any intervention of an imaging instruction from the operator between the X-ray Talbot imaging and the normal X-ray imaging.

8. An X-ray imaging system, comprising:

an X-ray Talbot imaging apparatus which includes an X-ray source, a plurality of gratings and an X-ray detector aligned in an X-ray radiation axis and which emits an X-ray from the X-ray source to the X-ray detector through a subject and the plurality of gratings to take a moire image with the X-ray detector; and an image processing apparatus which generates a plurality of reconstruction images from the moire image taken by the X-ray Talbot imaging apparatus, in which the plurality of reconstruction images includes at least three images of a differential phase image, an absorption image and a small-angle scattering image, wherein the X-ray Talbot imaging apparatus includes a retractor which retracts the plurality of gratings from an X-ray path, and wherein the X-ray imaging system performs:

X-ray Talbot imaging which includes setting an exposure energy of the X-ray Talbot imaging apparatus to a first exposure energy and taking the moire image with the X-ray detector; and normal X-ray imaging which includes retracting the plurality of gratings from the X-ray path by the retractor, setting the exposure energy of the X-ray Talbot imaging apparatus to the second exposure energy and emitting an X-ray from the X-ray source to the X-ray detector through the subject to take an absorption contrast image with the X-ray detector by normal X-ray imaging.

9. The X-ray imaging system according to claim 8, further comprising:

a rotator which changes a direction of the subject by rotating the subject about an axis of the X-ray, wherein the plurality of gratings includes a one-dimensional grating.

10. The X-ray imaging system according to claim 8, wherein the plurality of reconstruction images and the image obtained by the normal X-ray imaging are displayed on a screen in a same size.

11. The X-ray imaging system according to claim 8, wherein the second exposure energy is greater than the first exposure energy.

12. The X-ray imaging system according to claim 8, further comprising:

a controller which controls the X-ray Talbot imaging and the normal X-ray imaging, wherein the controller receives from an operator a successive imaging instruction to successively perform the X-ray Talbot imaging and the normal X-ray imaging, and wherein in response to the single successive radiographing instruction, the controller controls the X-ray Talbot imaging apparatus to successively perform the X-ray Talbot imaging and the normal X-ray imaging without any intervention of an imaging instruction from the operator between the X-ray Talbot imaging and the normal X-ray imaging.

* * * * *